United States Patent [19]

Cale, Jr.

[11] 4,087,428

[45] May 2, 1978

[54] N-(1-SUBSTITUTED-3-PYRROLIDINYL)-4-QUINOLINE CARBOXAMIDES

[75] Inventor: Albert Duncan Cale, Jr., Mechanicsville, Va.

[73] Assignee: A. H. Robins Company, Inc., Richmond, Va.

[21] Appl. No.: 683,604

[22] Filed: May 5, 1976

Related U.S. Application Data

[62] Division of Ser. No. 536,514, Dec. 26, 1974, Pat. No. 4,002,757.

[51] Int. Cl.² .......................................... C07D 401/12
[52] U.S. Cl. ................................. 260/287 F; 424/258
[58] Field of Search ..................................... 260/287 F

[56] References Cited

U.S. PATENT DOCUMENTS

| 1,825,623 | 9/1931 | Miescher | 260/287 F |
| 3,829,434 | 8/1974 | Evanega et al. | 260/287 F |

*Primary Examiner*—Donald G. Daus
*Assistant Examiner*—David E. Wheeler

[57] ABSTRACT

Novel N-(1-substituted-3-pyrrolidinyl)-1-naphthalene- and 4-quinolinecarboxamides of the formula:

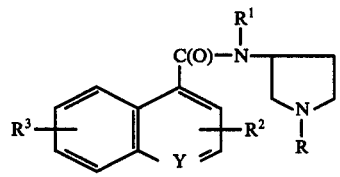

wherein R is lower cycloalkyl, $R^1$ is hydrogen, lower alkyl or aryl, $R^2$ is hydrogen, lower-alkyl, halogen, lower-alkoxy, amino or nitro, $R^3$ is hydrogen, lower-alkyl, halogen, lower-alkoxy, amino or nitro, Y is carbon or nitrogen and pharmaceutically acceptable acid addition salts thereof having anti-emetic properties are disclosed.

6 Claims, No Drawings

N-(1-SUBSTITUTED-3-PYRROLIDINYL)-4-QUINOLINE CARBOXAMIDES

This is a division of application Ser. No. 536,514 filed Dec. 26, 1974 now U.S. Pat. No. 4,002,757.

FIELD OF INVENTION

The present invention relates to certain novel 1-naphthalene- and 4-quinolinecarboxamides and is more particularly concerned with N-(1-substituted-3-pyrrolidinyl)-1-naphthalene- and 4-quinolinecarboxamides, compositions containing the same as active ingredients and methods of making and using them.

The prior art most closely related to the present invention and from which the present invention can be distinguished is U.S. Pat. No. 3,342,826 and U.S. Pat. No. 3,577,440. U.S. Pat. No. 3,342,826 discloses 2-(and 3-)benzamido- and 2-(and 3-)benzamidomethylpyrrolidines and piperidines. U.S. Pat. No. 3,577,440 discloses 3-propionamido and 3-benzamidopyrrolidine. The present invention is concerned with novel compounds wherein the amido moiety is a fused ring amido radical whereas the amido moiety of the prior art compounds are benzamido and propionamido radicals.

SUMMARY OF INVENTION

The invention is particularly concerned with 1-naphthalene- and 4-quinolinecarboxamides represented by the following general structural formula:

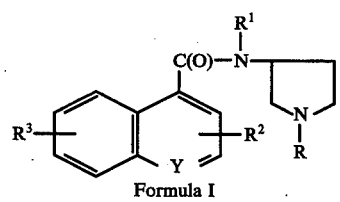

Formula I wherein;
R is lower cycloalkyl,
$R^1$ is hydrogen, lower-alkyl or aryl,
$R^2$ is hydrogen, halogen, lower-alkyl, lower-alkoxy, amino or nitro,
$R^3$ is hydrogen, halogen, lower-alkyl, lower-alkoxy, amino or nitro,
Y is carbon or nitrogen, and pharmaceutically acceptable acid addition salts thereof.

DETAILED DESCRIPTION OF INVENTION

The novel compounds of the invention having the foregoing Formula I are generally characterized by important pharmacological activity and are effective as anti-emetic agents and, as such, are particularly useful in controlling emesis in a living animal body.

The anti-emetic properties of the novel compounds of the present invention were demonstrated in dogs. The procedures used were a modification of the methods of Chen and Ensor, J. Pharm. Exp. Therap. 98, 245–50 (1950) and Leonard et al., J. Pharmac. Exp. Therap. 154, 339–45 (1966). The preferred compounds of the invention are those of Examples 2 and 3, respectively, namely, N-(1-cyclohexyl-3-pyrrolidinyl)-2-chloro-4-quinolinecarboxamide and N-(1-cyclohexyl-3-pyrrolidinyl)-1-naphthalenecarboxamide. The $ED_{50}$ of both examples is 1.2 mg/kg.

The non-toxic pharmaceutically acceptable acid addition salts of the compounds of Formula I are also included within the scope of this invention, since such salts are likewise useful for use as anti-emetics. Such salts are easily prepared by methods known to the art. Both organic and inorganic acids can be employed to form the pharmaceutically acceptable acid addition salts, illustrative acids being sulfuric, nitric, phosphoric, citric, acetic, lactic, tartaric, sulfamic, succinic, fumaric, maleic, hydrochloric, hydrobromic, benzoic and the like.

It is, therefore, a primary object of the present invention to provide novel N-(1-substituted-3-pyrrolidinyl)-1-naphthalene- and 4-quinolinecarboxamides. Another object is to provide a method for preparing the novel N-(1-substituted-3-pyrrolidinyl)-1-naphthalene- and 4-quinolinecarboxamides. A still further object is to provide novel compositions containing the N-(1-substituted-3-pyrrolidinyl)-1-naphthalene- and 4-quinolinecarboxamides and methods for their use as anti-emetic agents.

Additional objects and advantages of the present invention will be apparent to one skilled in the art and still others will become apparent from the following description of the best mode of carrying out the present invention thereof and from the appended claims.

In the definition of the symbols in Formula I given above, and where they appear elsewhere throughout the claims and specification hereof, the terms have the following significance.

The term "lower cycloalkyl" as used herein includes primarily cyclic alkyl radicals containing three up to nine carbon atoms inclusive and encompasses such groups as cyclopropyl, cyclobutyl, cyclopentyl, ethylcyclopentyl, cyclohexyl, methylcyclohexyl, propylcyclohexyl, cycloheptyl and cyclooctyl. The cyclohexyl radical represents a preferred radical.

The term "aryl" as used herein refers to an aryl radical of the benzene series, having six ring carbon atoms, and this term includes the unsubstituted phenyl radical and phenyl radicals substituted by any radical or radicals which are not reactive or otherwise interfering under conditions of the reaction, such as nitro, lower-alkyl, lower-alkoxy, trifluoromethyl, halo and the like. The substituted-phenyl radicals have preferably no more than one to three substituents such as those given above, and furthermore, these substituents can be in various positions of the phenyl nucleus and, where more than one substituent is present, can be the same or different and can be in various position combinations relative to each other.

When halogen is referred to herein, a halogen atom of atomic weight less than 80 is preferred.

The term "lower-alkyl" includes straight and branched chain radicals containing 1 to 8 carbon atoms as, for example, methyl, ethyl, propyl, isopropyl, n-butyl, isobutyl, tertiary butyl, amyl, isoamyl, n-hexyl, n-heptyl, and n-octyl radicals. A lower alkoxy group has the formula —O-lower alkyl.

In general, the novel compounds of this invention are prepared by acylating appropriate 1-substituted-3-aminopyrrolidines (III) whith a 1-naphthalenecarbonyl chloride or a 4-quinolinecarbonyl chloride (II) to give the corresponding 1-naphthalene-carboxamides and 4-quinolinecarboxamides embraced by Formula I. The reaction sequence is illustrated by the following:

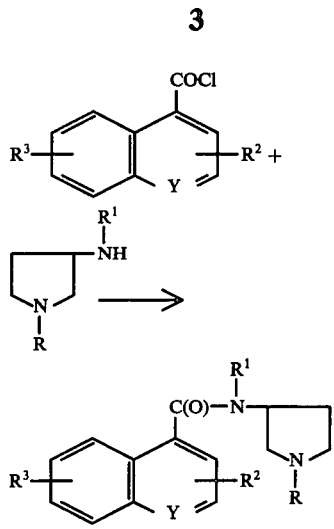

wherein R, R¹, R², R³ and Y are as defined hereinabove, except that R² or R³ cannot be amino.

Compounds of Formula I wherein R² or R³ is primary amino (—NH₂) are prepared by catalytic hydrogenation of the precursor nitro compound.

The 1-substituted-3-aminopyrrolidine starting materials of Formula III wherein R¹ is other than hydrogen are prepared according to methods disclosed in U.S. Pat. No. 3,337,580. Generally, a 1-substituted-3-pyrrolidinol is converted to a 1-substituted-3-halo-, a 3-alkylsulfonyloxy-, or a 3-aroylsulfonyloxypyrrolidine which is then reacted with a primary aromatic amine as, for example, aniline or a substituted aniline, or with non-aromatic primary amines including cyclohexylamine, cyclopentylamine, methylamine, ethylamine, isopropylamine, n-butylamine, and the like. The preparation of 1-substituted-3-halopyrrolidines is disclosed in U.S. Pat. No. 3,318,908.

The 1-substituted-3-aminopyrrolidine starting materials of Formula III wherein R¹ is hydrogen are prepared by reacting a 1-substituted-3-halopyrrolidine, preferably a 1-substituted-3-bromopyrrolidine with aqueous ammonia or with aqueous ammonia-lower alkanol solution at temperatures up to 150° C.

The 1-naphthalenecarbonyl chlorides and the 4-quinolinecarbonyl chlorides used as reactants in preparing the novel compounds of the present invention are prepared by reacting the precursor acids with thionyl chloride or when 2-chloro-4-quinolinecarbonyl chloride is used by reacting 2-hydroxy-4-quinolinecarboxylic acid with a mixture of phosphorous pentachloride and phosphorous oxychloride according to procedures well known to the art.

A suitable general procedure for preparing the N-(1-substituted-3-pyrrolidinyl)-1-naphthalene- and 4-quinolinecarboxamides of this invention, using the starting materials given above is as follows.

A solution of an acid chloride in a suitable organic solvent as, for example, chloroform, benzene, toluene, or the like, is treated dropwise with a solution of the 1-substituted-3-aminopyrrolidine in a like solvent. Alternately, the amine can be added to the acid chloride. The reaction which is carried out at, or slightly above, room temperature is rapid and proceeds to completion within a short time, usually in a period of about one half hour to one hour. The product can be isolated from the reaction mixture in a variety of ways, including acid-base extraction of the reaction mixture, isolation of the product from the aqueous basic partition portion by extraction with a suitable solvent, drying over a drying agent as, for example, magnesium sulfate and concentration of the dried solution to give the product which can be isolated as the free base or converted to a suitable acid addition salt as, for example, the hydrochloride.

Compounds of Formula I, wherein R² is primary amino (—NH₂) are prepared by shaking the precursor nitro compound in about three atmospheres of hydrogen using palladium-on-charcoal catalyst to give the corresponding amino compound which is isolated and purified using methods generally known to the art.

Another aspect of this invention contemplates and provides a pharmaceutical preparation in unit dosage form adapted for administration to obtain an anti-emetic effect comprising per dosage unit, an anti-emetic effective, non-toxic amount within the range from about 1 to about 300 milligrams of at least one compound of Formula I as defined hereinabove, and a pharmaceutical diluent.

The foregoing is a general description of how to prepare the compounds of the invention. The following examples illustrate the preparation of specific compounds which shall not be construed as a limitation of the scope of the invention set forth in Formula I.

EXAMPLE 1

N-Methyl-N-(1-cyclohexyl-3-pyrrolidinyl)-2-chloro-4-quinolinecarboxamide Hydrochloride.

To 12.7 g. (0.07 mole) of 1-cyclohexyl-3-methylaminopyrrolidine in dry benzene was added dropwise with stirring 15 g. (0.07 mole) of 2-chloroquinoline-4-carbonyl chloride in dry benzene. After 0.5 hr. the solution was extracted with dilute hydrochloric acid and the acidic solution made basic with sodium hydroxide solution and extracted with benzene. The benzene extracts were dried over sodium sulfate and concentrated. The residue was chromatographed on an aluminum silicate column eluting with a mixture of acetone benzene progressing from pure benzene to 50% acetone-benzene. The fractions containing the desired product were concentrated and the residue crystallized as the hydrochloride salt from isopropyl ether. The salt was recrystallized from isobutyl methyl ketone. Yield 10 g. (36%); m.p. 230°-233° C.

Analysis: Calculated for $C_{21}H_{27}Cl_2N_3O$: C, 61.77; N, 6.66; N, 10.29 Found: C, 61.40; H, 6.74; N, 10.25

EXAMPLE 2

N-(1-Cyclohexyl-3-pyrrolidinyl)-2-chloro-4-quinolinecarboxamide.

To 3.16 gm. (0.0195 mole) of 3-amino-1-cyclohexyl-pyrrolidine in 50 ml. of chloroform was added dropwise a solution of 3.5 gm. (0.015 mole) of 2-chloro-4-quinolinecarbonyl chloride in 50 ml. of chloroform. The reaction mixture was concentrated under reduced pressure and the residue was partitioned between ethyl acetate containing 10% isopropyl ether and dilute hydrochloric acid. The separated acid layer was made basic with dilute sodium hydroxide solution and extracted with chloroform. The chloroform solution was dried over sodium sulfate, concentrated and the residue recrystallized twice from isopropyl ether-ethyl acetate. The product (0.7 gm.; 13%) melted at 127°-219° C.

Analysis: Calculated for $C_{20}H_{24}ClN_3O$: C, 67.12; H, 6.76; N, 11.74 Found: C, 66.29; H, 6.86; N, 11.64

EXAMPLE 3

N-(1-Cyclohexyl-3-pyrrolidinyl)-1-naphthalenecarboxamide.

To 9.69 gm. (0.06 mole) of 3-amino-1-cyclohexylpyrrolidine in 50 ml. of chloroform was added dropwise a solution of 8.4 gm. (0.046 mole) of 1-naphthalenecarbonyl chloride in 50 ml. of chloroform. The reaction mixture was concentrated under reduced pressure and the residue was partitioned between ethyl acetate containing 10% isopropyl ether and dilute hydrochloric acid. The separated acid layer was made basic with dilute sodium hydroxide solution and extracted with chloroform. The chloroform solution was dried over sodium sulfate, concentrated and the residue crystallized from ethyl acetate. The product weighed 3.8 gm. (25%) and melted at 119°–120° C.

Analysis: Calculated for $C_{21}H_{25}N_2O$: C, 78.22; H, 8.13; N, 8.69 Found: C, 78.22; H, 8.17; N, 8.54

EXAMPLE 4

N-(1-Cyclohexyl-3-pyrrolidinyl)-N-methyl-1-naphthalenecarboxamide Hydrochloride.

To 18.8 gm. (0.11 mole) of 1-cyclohexyl-3-methylaminopyrrolidine in dry benzene was added dropwise with stirring 19.0 gm. (0.10 mole) of 1-naphthalenecarbonyl chloride in dry benzene. The crystalline product which separated was collected and recrystallized from benzene to give 27.5 gm. (74%) of product which melted at 219°–221° C.

Analysis: Calculated for $C_{22}H_{29}N_2OCl$: C, 70.85; H, 7.84; N, 7.51 Found: C, 70.68; H, 7.86; N, 7.37

EXAMPLES 5–27

By following the manipulative procedures disclosed hereinabove and in the preceeding examples and using the appropriately substituted 3-aminopyrrolidine and various substituted 1-naphthalenecarbonyl chlorides and 4-quinolinecarbonyl chlorides, the following compounds useful in the practice of this invention are prepared:

N-(1-cyclopentyl-3-pyrrolidinyl)-1-naphthalenecarboxamide

N-(1-cyclopentyl-3-pyrrolidinyl)-N-methyl-1-naphthalenecarboxamide

N-(1-cyclopentyl-3-pyrrolidinyl)-2-chloro-4-quinolinecarboxamide

N-(1-cyclohexyl-3-pyrrolidinyl)-N-(p-chlorophenyl)-1-naphthalenecarboxamide

N-(1-cyclohexyl-3-pyrrolidinyl)-N-phenyl-1-naphthalenecarboxamide

N-(1-cyclohexyl-3-pyrrolidinyl)-N-methyl-7-methyl-4-quinolinecarboxamide

N-(1-cyclohexyl-3-pyrrolidinyl)-7-chloro-4-quinolinecarboxamide

N-(1-cyclohexyl-3-pyrrolidinyl)-N-methyl-7-chloro-4-quinolinecarboxamide

N-(1-cyclohexyl-3-pyrrolidinyl)-4-bromo-1-naphthalenecarboxamide

N-(1-cyclohexyl-3-pyrrolidinyl)-4-chloro-1-naphthalenecarboxamide

N-(1-cyclohexyl-3-pyrrolidinyl)-4-ethoxy-1-naphthalenecarboxamide

N-(1-cyclopentyl-3-pyrrolidinyl)-N-(m-trifluoromethylphenyl)-1-naphthalenecarboxamide N-(1-cyclopentyl-3-pyrrolidinyl)-N-ethyl-8-methyl-4-quinolinecarboxamide N-(1-cyclopentyl-3-pyrrolidinyl)-4-nitro-1-naphthalenecarboxamide N-(1-cyclopentyl)-3-pyrrolidinyl)-4-amino-1-naphthalenecarboxamide N-(1-cyclopentyl-3-pyrrolidinyl)-8-nitro-4-quinolinecarboxamide N-(1-cyclopentyl-3-pyrrolidinyl)-8-amino-4-quinolinecarboxamide N-(1-cyclohexyl-3-pyrrolidinyl)-N-methyl-8-nitro-4-quinolinecarboxamide N-(1-cyclohexyl-3-pyrrolidinyl)-N-phenyl-8-nitro-4-quinolinecarboxamide N-(1-cyclopentyl-3-pyrrolidinyl)-N-(p-chlorophenyl)-8-nitro-4-quinolinecarboxamide N-(1-cyclopentyl-3-pyrrolidinyl)-N-methyl-4-ethoxy-4-quinolinecarboxamide N-(1-cyclopentyl-3-pyrrolidinyl)-N-phenyl-4-ethoxy-4-quinolinecarboxamide N-(1-cyclohexyl-3-pyrrolidinyl)-N-(p-aminophenyl)-2-chloro-4-quinolinecarboxamide.

PHARMACOLOGY

As mentioned hereinabove the anti-emetic properties of the compounds of Formula I were established using a modification of the methods of Chen and Ensor, J. Pharmac. Exp. Therap. 98: 245–250 (1950) and of Leonard et al, J. Pharmac. Exp. Therap. 154, 339–345 (1966). Activity was assessed by the compound's ability to reduce the frequency of apomorphine-induced emesis in dogs. The dogs were prescreened for fairly constant emetic responses to the subcutaneous administration of 0.1 mg/kg. of apomorphine hydrochloride, and those which vomited five or more times in the 4-minute period after apomorphine administration were selected for drug studies.

Groups of three dogs were used in preliminary tests and for the determinations of time of peak drug effect. Dose response curves were usually obtained using four drug-treated groups; each group contained at least three dogs. The dogs were fed approximately 17 hours prior to a test. Drugs were administered and at suitable intervals the dogs received 0.1 mg/kg. of apomorphin hydrochloride subcutaneously. Frequency of emesis was determined during the next 40 minutes and emesis was counted as the actual expulsion of stomach contents.

In oral studies, drugs were administered in gelatin capsules (controls received an empty capsule). In the subcutaneous studies, drugs were administered in distilled water and/or polyethylene glycol-300.

Dogs were re-used at intervals of not less than 1 week. The $ED_{50}$ is the dose which reduces the frequency of emesis of drug treated dogs to a value 50% below that of controls. Mean frequency of emesis for each drug treated group was compared with a mean control value derived by pooling the prior control emetic frequencies for all dogs used on that test day. The difference is expressed as a percentage decrease relative to controls. The percent decrease in mean frequency of emesis for each drug-treated group (ordinate) was plotted against log dose (abscissa) on semi-log graph sheets. The $ED_{50}$ was calculated by the method of Goldstein (Biostatistics, An Introductory Test: Pages 156–161; The MacMillan Co., New York, 1964).

The pharmaceutical compositions of this invention comprise at least one compound of Formula I as defined hereinabove in an amount to provide effective anti-emetic action. The compositions contain from about 1.0 mg. to 100 mg. of active medicament per unit dose.

Preferably, the compositions contain from about 5 mg. to 100 mg. of medicament, advantageously from about 5 mg. to about 50 mg. per unit dose.

The pharmaceutical carrier employed in the composition can be either solid or liquid. Exemplary of solid carriers are lactose, magnesium, stearate, terra alba, sucrose, talc, stearic acid, gelatin, agar, pectin or acacia. Exemplary of liquid carriers are vegetable oils and water. Similarly, the carrier or diluent may include a sustained release material such as glyceryl monostearate or glyceryl distearate alone or with a wax.

A wide variety of pharmaceutical forms can be employed by methods well known to the art. Thus, if a solid carrier is used the composition can be tableted or prepared as a powder, a troche, a lozenge or a suppository. Gelatin capsules containing the medicament can also be prepared. If a liquid carrier is used, the composition can be in the form of a soft gelatin capsule, a liquid suspension or a syrup. Parenteral dosage forms are obtained by dissolving a water-soluble salt of the active anti-emetic agent in water or saline solution in a concentration such that 1 cc. of the solution contains from 1.0 mg. to 25 mg. of active anti-emetic agent. The solution can then be filled into single or multiple dose ampules.

The method in accordance with this invention comprises administering internally to warm blooded animals at least one of the anti-emetic agents disclosed herein or a non-toxic organic or inorganic acid addition salt thereof, preferably with a non-toxic pharmaceutical carrier such as described above, in an amount sufficient to control nausea and vomiting. The active anti-emetic agent is administered orally or parenterally in repeated doses until satisfactory response is obtained. The daily dosage is from about 10 mg. to about 300 mg. of active medicament, advantageously from about 20 mg. to 200 mg. When the method described above is carried out, nausea and vomiting is controlled rapidly and effectively.

What is claimed is:

1. A compound selected from N-(1-substituted-3-pyrrolidinyl)-4-quinolinecarboxamides having the formula:

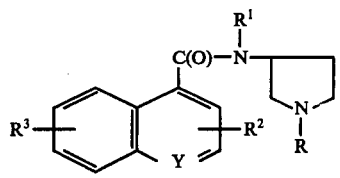

wherein;

R is lower cycloalkyl having 3 to 9 carbon atoms, $R^1$ is selected from the groups consisting of hydrogen, lower-alkyl having 1 to 8 carbon atoms, phenyl or substituted phenyl wherein one to three substituents are selected from halogen or atomic weight less than 80, lower-alkyl having 1 to 8 carbon atoms and lower alkoxy having 1 to 8 carbon atoms, $R^2$ is selected from the group consisting of hydrogen, lower-alkyl having 1 to 8 carbon atoms, halogen of atomic weight less than 80, lower-alkoxy having 1 to 8 carbon atoms, amino or nitro, $R^3$ is selected from the group consisting of hydrogen, lower-alkyl having 1 to 8 carbon atoms, lower-alkoxy having 1 to 8 carbon atoms, halogen atom of atomic weight less than 80, amino or nitro.

2. The compounds of claim 1 in the form of their pharmaceutically acceptable acid addition salts.

3. A compound of claim 1 which is N-methyl-N-(1-cyclohexyl-3-pyrrolidinyl)-2-chloro-4-quinolinecarboxamide.

4. A compound of claim 1 which is N-(1-cyclohexyl-3-pyrrolidinyl)-2-chloro-4-quinolinecarboxamide.

5. A compound of claim 2 which is N-methyl-N-(1-cyclohexyl-3-pyrrolidinyl)-2-chloro-4-quinolinecarboxamide hydrochloride.

6. A compound of claim 2 which is N-(1-cyclohexyl-3-pyrrolidinyl)-2-chloro-4-quinolinecarboxamide hydrochloride.

* * * * *

UNITED STATES PATENT AND TRADEMARK OFFICE
CERTIFICATE OF CORRECTION

PATENT NO. : 4,087,428
DATED : May 2, 1978
INVENTOR(S) : Albert Duncan Cale, Jr.

It is certified that error appears in the above-identified patent and that said Letters Patent are hereby corrected as shown below:

In claim 1 between lines 5 and 10, the formula should be

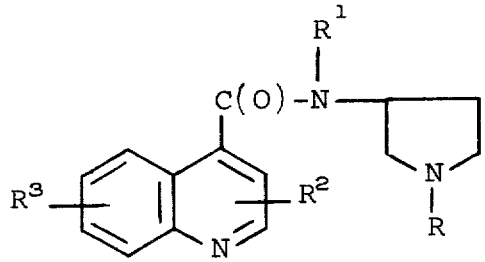

Signed and Sealed this

Fifth Day of September 1978

[SEAL]

Attest:

RUTH C. MASON
*Attesting Officer*

DONALD W. BANNER
*Commissioner of Patents and Trademarks*